United States Patent
Buck et al.

(10) Patent No.: US 12,185,656 B2
(45) Date of Patent: *Jan. 7, 2025

(54) MULTI-ZONE PROCESS AND APPARATUS FOR TREATING WASTEWATER

(71) Applicant: Cambrian Innovation, Inc., Watertown, CT (US)

(72) Inventors: Justin Buck, Auburndale, MA (US); Matthew Silver, Cambridge, MA (US); Zhen Huang, Newton, MA (US); Tzipora Wagner, Watertown, MA (US); Matthew Dorson, Arlington, MA (US)

( * ) Notice: Subject to any disclaimer, the term of this patent is extended or adjusted under 35 U.S.C. 154(b) by 215 days.

This patent is subject to a terminal disclaimer.

(21) Appl. No.: 17/746,824

(22) Filed: May 17, 2022

(65) Prior Publication Data

US 2022/0277561 A1    Sep. 1, 2022

Related U.S. Application Data

(63) Continuation of application No. 16/153,722, filed on Oct. 6, 2018, now Pat. No. 11,358,889.

(Continued)

(51) Int. Cl.
*A01C 21/00* (2006.01)
*G01N 33/00* (2006.01)
(Continued)

(52) U.S. Cl.
CPC ....... *A01C 21/007* (2013.01); *G01N 33/0036* (2013.01); *G01N 33/0098* (2013.01); *G01N 33/025* (2013.01); *G01N 33/24* (2013.01); *G05B 15/02* (2013.01); *G06F 18/22* (2023.01); *G06F 18/24* (2023.01); *G06T 7/0004* (2013.01);
(Continued)

(58) Field of Classification Search
CPC ............ A01C 21/007; G01N 33/0036; G01N 33/0098; G01N 33/025; G01N 33/24; G01N 2033/245; G05B 15/02; G06F 18/22; G06F 18/24; G06T 7/0004; G06T 2207/30188;
(Continued)

(56) References Cited

U.S. PATENT DOCUMENTS 5,217,788 A    6/1993    Rye
5,228,995 A    7/1993    Stover
(Continued)

FOREIGN PATENT DOCUMENTS

WO    WO2010147683    12/2010
WO    WO2012011984    1/2012
WO    WO-2015097648 A1 *    7/2015 .............. C02F 3/005

OTHER PUBLICATIONS

Machine-generated English translation of WO 2015/097648, generated on Feb. 29, 2024.*

(Continued)

*Primary Examiner* — Fred Prince
(74) *Attorney, Agent, or Firm* — Capital Patent + Trademark Law Firm, PLLC

(57) ABSTRACT

Wastewater containing organic matter may be treated using a multi-zone apparatus. In a first zone, organic matter in the wastewater may, among other things, be converted to at least volatile fatty acids (VFAs) and, thereafter, a portion of the treated wastewater may flow to a second zone that may, among other things, convert the VFAs to methane.

20 Claims, 8 Drawing Sheets

Related U.S. Application Data

(60) Provisional application No. 62/628,277, filed on Feb. 8, 2018, provisional application No. 62/569,001, filed on Oct. 6, 2017.

(51) Int. Cl.

| | |
|---|---|
| *G01N 33/02* | (2006.01) |
| *G01N 33/24* | (2006.01) |
| *G05B 15/02* | (2006.01) |
| *G06F 18/22* | (2023.01) |
| *G06F 18/24* | (2023.01) |
| *G06T 7/00* | (2017.01) |
| *G06V 20/10* | (2022.01) |
| *G06V 20/68* | (2022.01) |
| *H04W 4/02* | (2018.01) |
| *H04W 4/021* | (2018.01) |

(52) U.S. Cl.
CPC .......... *G06V 20/188* (2022.01); *H04W 4/021* (2013.01); *G01N 33/245* (2024.05); *G06T 2207/30188* (2013.01); *G06T 2207/30192* (2013.01); *G06V 20/68* (2022.01); *Y02A 40/28* (2018.01)

(58) Field of Classification Search
CPC ........ G06T 2207/30192; G06V 20/188; G06V 20/68; H04W 4/021; Y02A 40/28
USPC .......... 210/150, 615, 616, 617, 630, 748.01; 700/283
See application file for complete search history.

(56) References Cited

U.S. PATENT DOCUMENTS

| | | |
|---|---|---|
| 5,338,447 A | 8/1994 | Vellinga |
| 6,560,332 B1 | 5/2003 | Ainsworth et al. |
| 8,440,438 B2 | 5/2013 | Cheng et al. |
| 8,962,165 B2 | 2/2015 | Logan |
| 2005/0151281 A1 | 7/2005 | Tharp |
| 2012/0132521 A1 | 5/2012 | Silver et al. |
| 2013/0299400 A1 | 11/2013 | Silver et al. |
| 2014/0154754 A1 | 6/2014 | Stephens |
| 2014/0367330 A1 | 12/2014 | Liu et al. |
| 2015/0147593 A1 | 5/2015 | Silver et al. |

OTHER PUBLICATIONS

BIOPAQ IC, Anaerobic Industrial Effluent Treatment, Aug. 29, 2017, www.paques.nl.

Logan, Bruce E. et al., "Microbial Fuel Cells: Methodology and Technology", American Chemical Society, Published on Web Jul. 14, 2006.

Logan, Bruce E., "Scaling up microbial fuel cells and other bioelectrochemical systems", Appl. Microbiol Biotechnol (2010), 85:1665-1671.

\* cited by examiner

NOT WEIR SIDE

NON WEIR MIRROR

MULTI-ZONE PROCESS AND APPARATUS FOR TREATING WASTEWATER

RELATED APPLICATIONS

The present application is a continuation of, and claims priority to, U.S. patent application Ser. No. 16/153,722 filed Oct. 6, 2018 (the "'722 Application) and is related to U.S. patent application Ser. No. 13/811,132 filed Apr. 11, 2011 (the "'132 Application"), U.S. patent application Ser. No. 14/551,462 (the "'462 Application"), U.S. Provisional Application No. 62/515,472 filed Jun. 5, 2017 (the "'472 Application") and U.S. Provisional Application No. 62/569,001 (the "'001 Application") filed Oct. 6, 2017 and incorporates by reference the entire disclosures of the '722, '132, '462, '472 and '001 Applications as if each were set forth in full herein.

INTRODUCTION

Various reactors are available to treat water, particularly wastewater, from municipal, industrial, and agricultural sources. Such wastewater can require large amounts of energy to process, despite the fact that the wastewater can be a rich source of chemical energy. Reactors may contain biomass to aid in treating wastewater and can be operated aerobically or anaerobically.

Generally, anaerobic processes can involve a complex series of metabolic interactions among several groups of microorganisms, namely (i) hydrolytic bacteria, (ii) fermentative and acidogenic bacteria, (iii) acetogenic bacteria, and (iv) methanogens (e.g. aceticlastic and hydrogenotrophic bacteria and/or archaea). Anaerobic processes exhibit some advantages over aerobic processes. Particularly, anaerobic processes can be operated more efficiently with reduced operating costs and can recover some of the energy potential from the wastewater, sometimes in the form of methane.

However anaerobic processes can be unstable and subject to process upsets. As an example, changes in the organic loading rate can result in an accumulation of compounds, such as volatile fatty acid intermediates, interfering with other reactions, causing disruptions in other reactions, and incurring process upsets. In such circumstances, the reactor contents are emptied and discarded, and the reactor refilled and the microbes replaced, resulting in process interruptions and downtimes.

Furthermore, some anaerobic processes utilize conductive structures or electrodes that function to facilitate microbial reactions. Moreover, if maintenance or troubleshooting of the conductive structures or electrodes is required, accessing the structures requires shutting down the entire process.

Hence, there is a desire to improve the performance of anaerobic processes to overcome the deficiencies discussed above.

Additionally, at times, it is desirable to monitor and control the reactor and support systems locally and from remote locations under a variety of situations. These situations can include, but are not limited to, responding to upset or emergency conditions, operating the equipment by a third party, assisting on-site operations with troubleshooting, conducting troubleshooting for on-site operations, and operating in isolated geographical locations.

Accordingly, there is a desire to improve the monitoring of anaerobic processes.

SUMMARY

One exemplary embodiment is a process for treating wastewater. The process can include providing a first liquid stream to a first zone, passing at least a portion of the first liquid stream past the first bioreaction zone, sending at least a portion of the passed first liquid stream to a second zone that may include a plurality of electrodes having at least one anode and at least one cathode, and obtaining an effluent from the second zone and recycling at least a portion to the first zone. Generally, the first zone bioreaction zone may function to facilitate the growth of a first group of one or more microbes, while the plurality of electrodes in the second zone may function to facilitate the growth of a second group of one or more microbes. Often, at least a portion of the second group from the second zone is communicated to the first zone.

Moreover, the second group of microbes can include one or more "anode respiring microbes" capable of extracellular electron transfer to electrodes or other microbes, specifically one or more "anode respiring microbes" from the family Geobacteraceae, or more specifically one or more "anode respiring microbes" from the genus *Geobacter*, and in some embodiments from the species *Geobacter metallireducens*. Also, usually the one or more "anode respiring microbes" can associate with one or more aceticlastic or hydrogenotrophic methanogens. Furthermore, the second group of microbes can further include one or more methanogenic microbes, more specifically one or more archaea from the genus *Methanosarcina* and the genus *Methanosaeta*. What is more, the first group can include one or more microbes from at least one of the genus *Pseudomonas, Streptococcus*, and *Clostridium* and the family Enterobacteriaceae.

The process can further include heating at least the portion of the first liquid stream to the desired reactor temperature for the type of reactor (psychrophilic, mesophilic, or thermophilic). For mesophilic reactor conditions, this is about 30-about 45° C., more specifically to about 35-about 38° C. and an exemplary, non-limiting headspace pressure range about 90,000-about 110,000 Pa. Also, the process can further include heating at least the portion of the first liquid stream, and even further include combining an alkaline stream, optionally including sodium hydroxide, with the recycled effluent from the second vessel. Caustic or acid may be added to maintain the pH of the treatment zones in desired ranges, typically about 6.5 to 7.5, more specifically about 6.8-about 7.2.

Another exemplary embodiment is an apparatus for treating wastewater. The apparatus can include a first zone having a first vessel and a second zone having a second vessel. Generally, the first or second vessel may be adapted for receiving a first or second liquid stream and can include a bioreaction zone and a first or second compartment. Usually, a first bioreaction zone optionally has a first structure for facilitating retention or growth of one or more microbes and the associated compartment has a volume adapted to receive a liquid exiting the packing. Often, the first structure is a packing material that functions to facilitate the growth of one or more microbes. Moreover, the second vessel may be downstream from the first vessel and may be adapted to receive a stream from the first compartment. What is more, the second vessel can include a bioreaction zone ("second bioreaction zone") having a plurality of electrically conductive structures or electrodes, optionally vertically arranged, and a compartment ("second compartment") adapted to receive a liquid that passed the plurality of electrodes. The plurality of electrically conductive structures or electrodes may function to facilitate the growth of one or more microbes in the second vessel. The second vessel may be in communication with the first vessel that and function to facilitate the passage of the one or more microbes from the second vessel to the first vessel. Optionally, the second vessel may be directly downstream of the first vessel. Additionally, the apparatus can further include a heat exchanger for heating at least a portion of the first liquid stream entering the first vessel, and still further include an inline mixer upstream of the heat exchanger. Moreover, the first bioreaction zone of the first vessel can have a suspended growth retention structure or a fixed-film structure and the first vessel may have an anaerobic filter. The fixed-film structure may comprise a dynamic packing media, carrier material, or a statis packing media.

A further exemplary embodiment may be a process for treating wastewater. The process may include providing a first liquid stream to a first vessel having a packing that functions to facilitate the growth of a first group of one or more microbes from at least one of the genus *Pseudomonas*, *Streptococcus*, and *Clostridium*, and the family Enterobacteriaceae, passing the first liquid stream past the packing, sending the past first liquid stream to a second vessel, and obtaining an effluent from the second vessel and recycling at least a portion to the first vessel and communicating one or more anode respiring bacteria from the second vessel to the first vessel. Often, the second vessel has a plurality of electrodes including at least one anode and at least one cathode. Generally, the plurality of electrodes functions to facilitate the growth of a second group of one or more microbes having one or more anode respiring bacteria.

In addition to the apparatuses and processes described above, the present invention further discloses a second vessel that may include one or more electrodes and insulated separators received by one or more guidepieces such that a given separator is positioned between pairs of electrodes. In embodiments, each of the guidepieces may have a vertical length that equals the vertical length of an electrode 340 (e.g., 8 feet).

In an embodiment, each of the electrodes and separators may be of a sufficient weight so that they are retained within a respective slot of a guidepiece without the need for additional retaining means. Alternatively, the guidepieces may include additional structure to allow a received electrode or separator to be retained and removed (e.g., clips, pressure sensitive bindings, clamps).

In an embodiment, a guidepiece may further comprise a means for separating each of the electrodes or separators. In one example, each separating means may comprise a section of the guidepiece that protrudes substantially perpendicular from a main section of the guidepiece. Further, the dimensions of a separation may comprise a dimension (width) that separates a separator from an electrode and optimizes the flow of treated wastewater through the second vessel. In one embodiment a guidepiece may comprise a multipiece element (e.g., two elements).

An exemplary second vessel may include one or more weirs that function to apply a force to, and distribute energy in, flowing wastewater.

In yet another embodiment, an exemplary apparatus may comprise a support structure that may be integral to standpipe. In those instances where the pressure exerted by wastewater within the second vessel may exceed the pressure exerted by wastewater within the standpipe, the support structure functions to provide support for the external wall of the second vessel, as well as functioning as a wall of the standpipe, where it should be understood that the external wall of the second vessel and standpipe wall may be one and the same structure.

Still further, another exemplary apparatus for treating wastewater may comprise: a first zone adapted for receiving a first liquid stream and comprising a first bioreaction zone, wherein the first bioreaction zone is configured with one or more first structures for retaining or facilitating growth of one or more first biological microbes and for at least converting organic matter in the first liquid stream into at least volatile fatty acids (VFAs) to produce treated wastewater; a second zone for receiving the treated wastewater from the first zone, said second zone comprising a second bioreaction zone comprising a plurality of second structures configured to facilitate growth of one or more second biological microbes, wherein said plurality of second structures are electrically conductive for further treating the wastewater and at least converting the VFAs into methane. It should be understood the second zone may be in communication with the first zone to facilitate passage of the one or more microbes in the second zone from the second zone to the first zone. The second zone may, or may not be, configured downstream from the first zone.

It should be understood that first and second zones may be configured in the same vessel, or in different vessels.

The exemplary apparatus may further comprise first means for mixing or fluidizing biomass or dynamic media structures in zone one and/or a second means for mixing in zone two. The first means for mixing or fluidizing may comprise means selected from the group comprising a mechanical mixer, liquid recirculation mixer or jet mixer or gas mixer, while the second means for mixing may comprise liquid recirculation flow structure or a gas mixer.

In addition to the means for mixing/fluidizing, the exemplary apparatus may comprise a manifold operable to: receive a biogas stream for mixing and stripping organic growth from one or both of the first or and/or second structures; distribute or collect fluid at the top of the first zone or at the bottom of the first zone; and/or distribute or collect fluid at the top of the second zone or at the bottom of the second zone.

The liquid entering the first zone may be a wastewater stream and the first zone may be further adapted to receive a mixed stream comprising previously further treated wastewater from the second zone as well.

In a variation of the exemplary apparatus, the one or more first structures may comprise a suspended growth retention structure or fixed-film structure (e.g., dynamic media, or carrier material or statis packing media). Further, the first zone may further comprise a first compartment configured to receive treated wastewater exiting the first structures for transport to the second zone. The second zone may also comprise a second compartment configured to receive treated wastewater exiting the second structures for transport out of the system or return to the first zone.

In an alternative embodiment the plurality of second structures may be vertically arranged, may comprise a porous mesh or, alternatively may comprise a plurality of electrodes, for example where the electrodes may also be vertically arranged and/or comprise a porous mesh. The structures may also be arranged horizontally, at various uniform angles, or randomly arranged with the zone.

To retain and support the second structures the second zone may comprise one or more guidepieces for retaining one or more of the second structures, where one or more of the guidepieces may comprise additional structure configured to retain and remove one or more of the second structures.

In addition to the exemplary embodiments above the present invention also provides for similar apparatuses that comprise one or more of the following features: (i) an apparatus where the pH and temperature in the first and second zones are maintained at the same levels, e.g., a pH of between 5 and 9, and a temperature between 25° C. and 41° C.; (ii) an apparatus where the pH and temperature in the first and second zones are maintained at different levels, e.g., a pH of between 5 and 7 and a temperature between 15° C. and 41° C. in the first zone, while a pH of between 6.5 and 8, and a temperature between 35° C. and 38° C. in the second zone; (iii) a compartment configured to receive treated wastewater exiting the first zone and for transport to the second zone, and/or a compartment configured to receive wastewater exiting the second zone; (iv) a packing in the first zone; (v) a heat exchanger, and a chemical injection apparatus and an inline mixer, wherein the chemical injection apparatus and inline mixer may be upstream of the heat exchanger; (vi) one or more guidepieces for retaining one or more second structures (e.g., electrodes, porous mesh); (vii) means for separating, that may comprise one or more separators that may be positioned between pairs of electrodes of the plurality of electrodes, where a vertical length of each of the guidepieces equals a vertical length of each of the second structures (e.g. electrodes); (viii) where one or more of the guidepieces comprises additional structure configured to retain and remove one or more of the second structures (e.g., electrodes) or separators, some examples of such additional structure being clips, pressure sensitive bindings, and clamps, for example and (ix) one or more guidepieces may additionally comprise guidepiece means for separating (e.g., a section of a guidepiece protruding substantially perpendicular from a main section of the guidepiece), where such a means may have a width that separates a second structure and/or insulated separator from another structure and optimizes flow of treated wastewater through the second vessel.

In embodiments of the invention the one or more guidepieces may comprise a multipiece element, for example.

A further exemplary apparatus may comprise one or more of the features described above and herein, and, in addition may comprise one or more weirs for distributing energy in received, treated wastewater in the second zone, and a support structure.

In addition to the apparatuses set forth above and herein, the present invention also provides for processes (or methods, collectively referred to as "processes") that parallel the apparatus and their associated functions. For the sake of understanding, such processes shall not be repeated here though it should be understood that such processes may be readily determined by those skilled in the art from an understanding of the apparatuses and functions described above and the text and drawings herein.

These and other features and advantages will be more clearly understood from the following detailed description taken in conjunction with the accompanying drawings.

BRIEF DESCRIPTION OF THE DRAWINGS

For a more complete understanding of the present disclosure and the advantages thereof, reference is now made to the following brief description, taken in connection with the accompanying drawings and detailed description, wherein like reference numerals represent like parts.

DEFINITIONS

Figure 1:
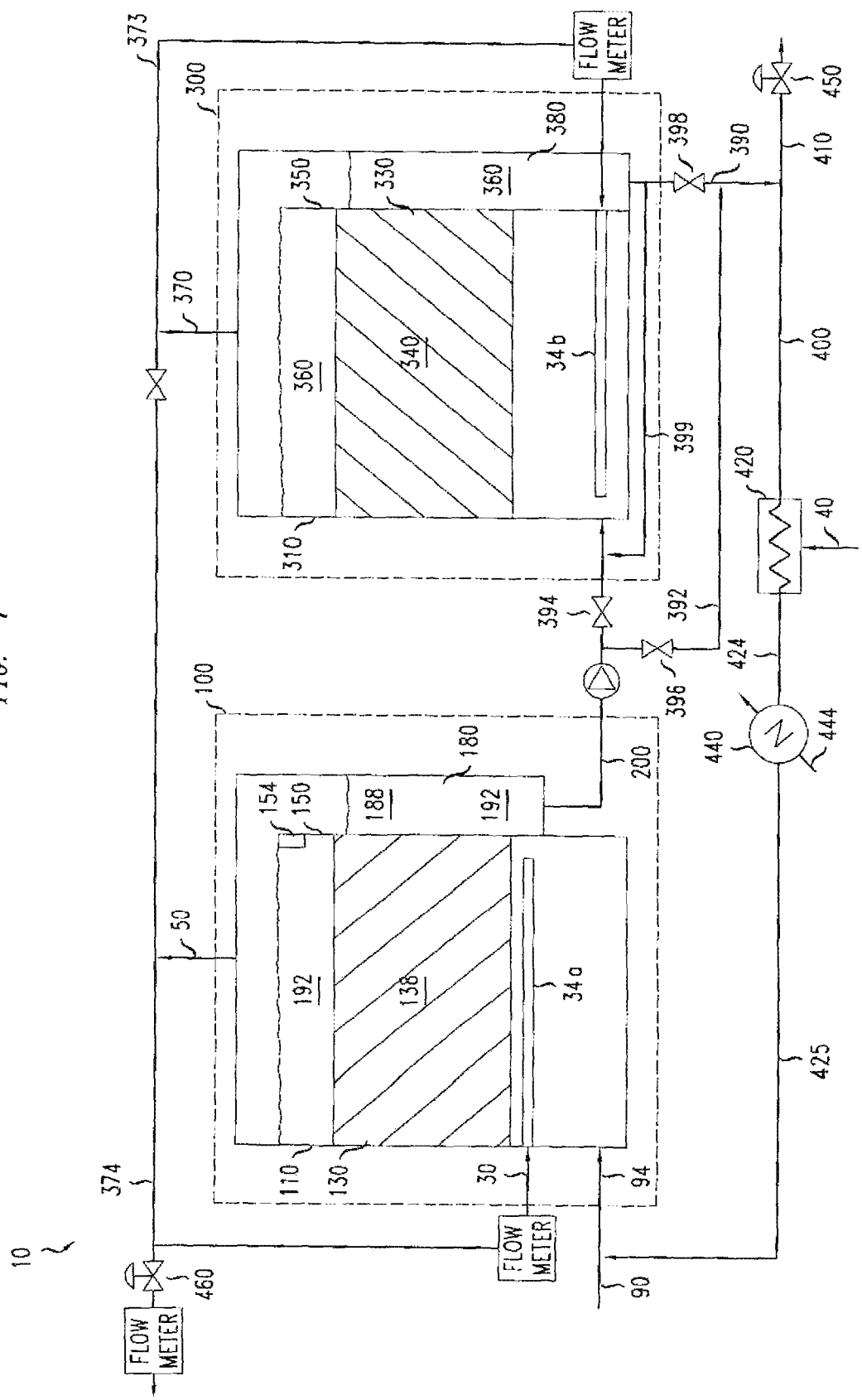
FIG. 1 is a schematic depiction of an exemplary apparatus.

As used herein, the words "comprising", and any form thereof such as "comprise" and "comprises"; "having", and any form thereof such as "have" and "has"; "including", and any form thereof such as "includes" and "include"; and "containing" and any form thereof such as "contains" and "contain" are inclusive or open-ended and do not exclude additional, unrecited elements or process steps.

As used herein, the term "stream" can include various molecules in liquid or gas state, and can include mixtures of gases, liquids, and particulate solids. Generally, a stream can be a wastewater stream or a biogas stream containing methane.

As used herein, the term "zone" can refer to an area including one or more structural items and/or one or more sub-zones. Some non-limiting examples of structural items are: reactors, reactor vessels, vessels, heaters, exchangers, pipes, pumps, compressors, electrically conductive structures (e.g., electrodes, porous mesh) controllers, mixers, manifolds, suspended growth retention structures, fixed-film structures (e.g., a dynamic packing media ("packing" for short), carrier material, or a statis packing media) and additional structure for facilitating retention or growth of one or more microbes. Additionally, a structural item, such as a reactor, dryer, or vessel, can further include one or more zones or sub-zones. Optionally, a zone can be identified by the presence of a packing media, a suspended region of biomass, aeration, and/or phase difference, for example.

As used herein, the term "communication" can mean material flow operatively permitted between enumerated components.

As used herein, the term "downstream" can mean at least a portion of material that flows to a "subject" (destination) may operatively flow from an "object" (source) with which the subject communicates. Generally, recycled material is not considered when referencing the term "downstream".

As used herein, the term "upstream" can mean the opposite of downstream, such as at least a portion of material that flows from the subject to the object with which it communicates. Generally, recycled material is not considered when referencing the term "upstream".

As used herein, the term "direct" or "directly" can mean a flow from an upstream component that enters a downstream component without undergoing a compositional change due to physical purification, such as flashing, fractionating, absorbing, adsorbing, or extracting, or chemical conversion, such as reacting. However, a stream can be communicated directly if it undergoes heating or cooling through, e.g., an exchanger, passed through a pump or compressor, or subject to a pH change through chemical or nutrient addition.

The phrases "adapted to" and "operable to" used herein mean "functions to" unless the context dictates otherwise.

As depicted, process flow lines in the figures can be referred to interchangeably as, e.g., lines, pipes, feeds, influents, effluents, portions, reactants, products, or streams.

As used herein, the term "wastewater" can mean water containing dissolved organics obtained from at least one of agricultural or farm, food processing, petrochemical, beverage, dye, textile, residential or domestic, and pharmaceutical facilities or sources, for example.

As used herein, the term "volatile fatty acids" can be abbreviated "VFA" and can include fatty acids up to six carbon atoms, and salts, anions, isomers, and esters thereof. VFA can include methanoic acid, ethanoic acid, propanoic acid, butanoic acid, pentanoic acid, and salts, anions, isomers, and esters thereof, hydrogen, carbon dioxide, ethanol, ammonia or azane, and propan-2-one or acetone. Additionally, methanoic can be referred to as "acetic" and pentanoic can be referred to as "valeric".

As used herein, the term "acetate" can include a salt of acetic acid where the hydrogen atom is replaced by a metal, an ester of acetic acid, and anion of acetic acid.

As used herein, the terms "electrically active microbes" can mean microbes that engage in electron exchange to or from a cell.

As used herein, the terms "extracellular electron transfer" can be abbreviated "EET" and mean the transfer of electrons outside a cell to a receiving body, such as an electrode, a metal deposit, and/or another microbe.

As used herein, the term "electrogen" or "electricigen" can mean one or more microbes generating an electric current.

As used herein, the terms "anode respiring microbe" can mean a microbe specific to an anode reaction, to consumption of a substrate, and to transfer of electrons to the anode via a respiration coupled process.

As used herein, the term "electromethanogens" can mean a methanogen utilizing free electrons, donated from electrode or another microbe, for producing methane.

As used herein, the terms "syntrophic acetate oxidation" can be abbreviated "SAO" and mean two different microbial species interacting to convert acetate to methane through a variety of coupling mechanisms for mass and energy transfer.

As used herein, the terms "direct interspecies electron transfer" can be abbreviated "DIET" and mean EET between two microbes optionally during SAO.

As used herein, the terms "interspecies hydrogen transfer" can be abbreviated "IHT" and mean a form of SAO using the transfer of molecular hydrogen gas.

As used herein, the term "dynamic media" may be used interchangeably with "carrier material", or "packing" or "packing media". Any of these terms means a material of any size, shape, material, or density incorporated into a treatment unit for the purpose of facilitating microbial attachment and retention within the treatment zone.

As used herein, the term "electrically conductive" or "structure that are electrically conductive" means a material of sufficient electrical conductivity to transfer electrons from one region to an adjacent region. For example, materials having a resistivity of $<\sim 1\times 10^{-2}$ ohm-meter or conductivity of $>\sim 10$ S/m may be electrically conductive depending on their configuration.

As used herein, the term "microbe" or "microorganism" can mean a microscopic organism, either single-celled or multicellular, usually single-celled, of an animal, a plant, a fungus, a protist, a bacterium, an archaeon, or a eukaryote, usually a bacterium, an archaeon, or a eukaryote.

As used herein, the term "group" can include at least one item, sometimes more than one, of same or different items. As an example, a group can include at least one microbe or a plurality of microbes being the same or different organisms, such as different species, and one group of microbes can include microbes the same or different from another group of microbes at a different location. Thus, one group can be distinguished from another group by being at a different location. It should be understood the that the meaning, and use of the term "group", in reference to microbes herein is distinct and different from the use of the term "group" to describe a phylogenetic group and taxonomic classification.

The word "bioreaction" as used herein includes at least processes that involve a biological agent as part of the reaction as a reactant, product, or catalyst.

It should be noted that to the extent dimensions, pressures, pHs, temperatures and other values are described in the text or shown in figures, such values are merely exemplary, and are provided to give those skilled in the art an example(s) of the relative values of a respective embodiment(s) of the invention.

As used herein, the term "about" or "approximately" is defined as being close to or near as understood by one of ordinary skill in the art, and in some embodiments, may be quantified as within 90%, particularly within 50%, more particularly within 10%, even more particularly within 5%, still more particularly within 1%, and is in some cases within 0.5%.

As used herein, the term "a" or "an" when used in conjunction with the term "comprising" or a form thereof may mean "one", but is also consistent with the meaning of "one or more", "at least one", and "one or more than one".

As used herein, the term "Pascal" may be abbreviated "Pa", the terms "meter-squared" may be abbreviated "$m^2$", the terms "meter-cubed" may be abbreviated "$m^3$", the terms "biological oxygen demand" or "biochemical oxygen demand" may be abbreviated "BOD", the terms "chemical oxygen demand" may be abbreviated "COD", and the terms "degrees Celsius" may be abbreviated "° C.". All pressures are absolute.

As used herein the phrases "embodiment' or "exemplary" mean one example of the present invention.

Detailed Description, with Examples

It should be understood at the outset that although exemplary implementations of embodiments of the present invention are described herein, the present system may be implemented using any number of techniques, whether currently known or in existence. The present disclosure should in no way be limited to the exemplary implementations, drawings, and techniques described herein, including the exemplary designs and implementations described herein and illustrated in the drawings, but may be modified with their full scope of equivalents.

Although not wanting to be bound by theory, an anaerobic process or digestion can include several metabolic interactions, usually associated with microbes, such as hydrolysis, acidogenesis, acetogensis, and methanogenesis. Sometimes, at least some of these processes occur within a single vessel.

Usually, anaerobic digestion uses microbial species that occupy different niches, roughly divided into two groups based on their metabolisms. The acid-former group, which contains many sub-niches, includes species that digest polysaccharides, sugars, fatty acids, alcohols and more complex molecules in the waste into organic acids, primarily acetate, but also others like lactate and butyrate. Sometimes, the second class is the methane-formers, or methanogens, which may include two sub-niches. Some methanogens can metabolize acetate directly and produce methane as a byproduct (aceticlastic methanogenesis), while other methanogenic species may combine hydrogen as an electron donor with carbon dioxide to produce methane (hydrogenotrophic methanogenesis).

Although not wanting to be bound by theory, in aceticlastic methanogenesis, for each molecule of acetate consumed, often equal amounts of carbon dioxide and methane are produced. In hydrogenotrophic methanogenesis, for every four molecules of hydrogen gas consumed, sometimes one molecule of carbon dioxide is also consumed to produce methane and two molecules of water. Generally, while aceticlastic methanogenesis produces carbon dioxide, the hydrogenotrophic process effects a net decrease in carbon dioxide. A discussion of anaerobic digestion is disclosed in, e.g., the '132 application, the disclosure of which is incorporated herein as if set forth in full herein.

However, a sudden increase in the organic loading rate can result in an increase in VFA, which may interfere with other reactions in a vessel. Such interference can lead to upsets, and in some instances, cause a complete disruption requiring shutting down of a process and replacement of the microbes metabolizing reactions. Sometimes, at least some of the VFA are converted to acetate via acetogenesis, the acetate is converted to methane by aceticlastic methanogens.

TABLE 1

Temperature Ranges of Anaerobic Treatment

| AD Reactor Type | Temperature Range | Applications |
| --- | --- | --- |
| psychrophilic | 12-16° C. | in landfills, swamps or sediments |
| mesophilic | 35-37° C. | in the rumen and in anaerobic digester |
| thermophilic | 55-60° C. | anaerobic digesters or geothermally heated ecosystems |

Although not wanting to be bound by theory, anaerobic treatment can traditionally be maintained at three different temperature ranges (see Table 1). The anaerobic mesophilic process is the most widely used. Though thermophilic anaerobic fermentation has its disadvantages, such as reduced process stability, reduced dewatering properties of fermented sludge and the requirement for large amounts of energy for heating, it has the significant advantage of the thermal destruction of pathogenic bacteria at elevated temperatures. The slightly higher rates of hydrolysis and fermentation under thermophilic conditions have not led to a higher methane yield, that is to say that no significant change in a total methane yield from organic matter for fermentation temperatures ranging from 30° C. to 60° C. has been reported. Finally, psychrophilic systems typically have slower rates of treatment.

Although not wanting to be bound by theory, the optimal temperatures for the survival of thermophilic and mesophilic bacteria are 55° C. and 35° C., respectively, however a wide range of temperatures can be maintained in functioning systems. It has been suggested that gas production during anaerobic digestion is related to temperatures. It has been reported that gas production was linearly correlated with temperature from 25 to 44° C., which was between 0.26 and 0.42 CH4 m3/kg total solids (TS). However, other researchers suggested that an increase in the temperature resulted in a reduction of the biogas yield, due to the increased inhibition of free ammonia (NH3) which increases with increasing temperature. Thus, the optimal temperature of an inventive apparatus described herein may depend on the waste stream to be treated, treatment objectives, and treatment system design. An optimal temperature for exoelectrogenic bacterium was found to be 30-35, but activity has been demonstrated at lower temperatures, such as 20° C. or even as low as 4° C. and into the thermophilic range up to 55° C. and above. Generally, methanogenic and acetogenic bacteria have a narrower range of optimum temperatures than the bacteria associated with hydrolysis and acidogenesis.

TABLE 2

General pH range of Anaerobic Microorganisms

| Microorganism | pH Range |
| --- | --- |
| Hydrolytic | 5.5-6.5 |
| Acidogenic | 5.5-6.5 |
| Acedogenic | 6.6-7.4 |
| Methanogenic | 6.5-8.0 (optimal: 6.8-7.2) |
| Exoelectrogenic | 7.0 |

Although not wanting to be bound by theory, microorganisms can be differentiated according to their optimal pH range (see Table 2). Methanogenic bacteria work effectively at the pH range of 6.5 and 8. However, for hydrolysis and acidogenisis, ranges between 5.5 and 6.5 have been reported to be optimal. For acetogenisis, the optimal pH range was 6.6 to 7.4. Anaerobic digestion may also be carried out at a neutral pH. The decrease in pH is due to the accumulation of carbon dioxide and volatile fatty acid as a result of digester overloading.

TABLE 3 pH range and sensitivity of several methanogenic genus

| Parameter | Methanosaeta | Methanosarcina |
| --- | --- | --- |
| pH range | 6.5-8.5 | 5.0-8.0 |
| pH Shock | <0.5 | <0.8-1.0 |

Although not wanting to be bound by theory, methanogenic Archaea are responsible for the final and critical step of anaerobic digestion, as they produce valuable methane. One of the major drawbacks of anaerobic digestion is however the sensitivity of the methanogenic consortium to different environmental factors. An abrupt change in pH often causes system failure. It has been reported that *Methanosarcina* sp. have high growth rates (i.e., doubling times in the order of 1.0 to 1.2 days) and are tolerant to sudden changes in pH of around 0.8-1.0 units caused by overloading, compared to *Methanosaeta*, which have doubling times of minimum 4-6 days and tend to be affected by a pH shock of 0.5 units or even less (see Table 3). Therefore, different inventive apparatuses have different ability to tolerate changes in pH based on the composition of the microbial community and the biochemical reactions being performed.

Although not wanting to be bound by theory, based on the relative balance of reactions for the treatment of a specific waste stream, it may be desirable to operate different treatment zones of the inventive apparatuses described herein at different temperatures or pH levels to encourage different microbial communities and biochemical reactions. Accordingly, in one embodiment it may be to operate a first zone at a lower pH to further encourage production of volatile fatty acids and a second zone at a higher pH to further encourage production of methane. It may also be desirable to operate the first zone at a lower temperature than the second zone if conditions are sufficient to facilitate desired reactions. Alternatively, it may be desirable to operate the first zone at a higher temperature than the second zone to accelerate hydrolysis and acidogenesis, among other reactions. In some instances, for process simplicity, it may be desirable to operate both zones of the vessel or reactor of an inventive apparatus at the same temperature and/or pH. In other instances, the individual zones may be run at different temperatures and/or pHs to optimize treatment rates, and limit the cost of inputs to the process.

Although not wanting to be bound by theory, by providing anode respiring bacteria another reaction pathway, namely syntrophic acetate oxidation, may allow a faster reaction of any accumulated acetate and minimize interference due to excess acetate accumulation. Also, a greater diversity of methanogenic microbes can create a more robust system able to withstand variations in operating conditions.

In one exemplary embodiment, one zone or vessel is provided for primarily conducting hydrolysis, acidogenesis, and acetogenesis, and a second zone or vessel is provided for primarily conducting methanogenesis via syntrophic acetate oxidation and aceticlastic methanogens. Additionally, methanogenesis can also be conducted in the first zone or vessel along with hydrolysis, acidogenesis, and acetogenesis. In some instances, at least one microbe from the second zone or vessel can be transferred in a recycle stream to the first zone or vessel that functions to facilitate preferred reactions, such as metabolizing acetate.

Referring to FIG. 1, an exemplary apparatus 10 may include a first zone 100 including a first vessel 110, a second zone 300 including a second vessel 310, and a first means for mixing or fluidizing biomass or dynamic media structures 420. While a single mixing and fluidizing means 420 is depicted in FIG. 1 it should be understood that the apparatus 10 may comprise more than one such means. For example, the first mixing and fluidizing means 420 may be within zone 100 while a second mixing means (not shown in FIG. 1) may be within zone 300. In embodiments, the first means may comprise means selected from the group comprising a mechanical mixer, liquid recirculation mixer, chemical injection apparatus or gas mixer, while the second means for mixing may comprise liquid recirculation flow structure or a gas mixer. The apparatus 10 may yet further comprise a heat exchanger 440 for heating at least a portion of the first liquid stream. In an embodiment, the chemical injection apparatus and inline mixer may be upstream of the heat exchanger 440.

Although two different vessels 110 and 310 are depicted, it should be understood that the first zone 100 and the second zone 300 can be contained within a single, same vessel optionally with any suitable partition instead of containing vessels 110 and 310. Further, while only a single first zone 100 and vessel 110 are depicted, it should be understood that more than one first zone 100 and/or more than one first vessel 110 (as described further herein) may be included, where each such first zone 100 and/or vessel 110 functions as described herein in conjunction with the second zone 300. In those embodiments that include more than one first zone 100 and/or vessel 110, it should be understood that such a combined apparatus may function as follows: (i) each of the plurality of first zones/vessels 100/110 may simultaneously function to treat wastewater as described herein, be coupled or otherwise connected to the second zone 300, and simultaneously provide their treated wastewater to the second zone 300; and (ii) each of the plurality of first zones/vessels 100/110 may simultaneously function to treat wastewater as described herein, be coupled or otherwise connected to the second zone 300, however, less than all of the first zones/vessels 100/110 simultaneously provide their treated wastewater to the second zone 300 (e.g., they provide their treated wastewater in some sequence). For example, in the simplest case where they are only two first zones/vessels 100/110, zone "A" and zone "B", the wastewater from zone A would be provided to the second zone 300 first, followed by the wastewater from zone B, or vice-versa.

Yet further, in other embodiments, each of the first zones or one or more of such zones/vessels 100/110 may function independently from the second zone 300 (i.e., wastewater from a first zone/vessel 100/110 is not provided to the second zone 300), or only a partial amount of the wastewater from one or more of the first zones/vessels 100/110 is provided to the second zone 300. The combined functions of the first and second zones set forth herein are merely illustrative, it being understood that other combined functions and related methods of operation fall within the scope of the present disclosure.

Similarly, while only a single second zone 300 and vessel 310 are depicted, it should be understood that more than one second zone 300 and/or more than one second vessel 310 (as described further herein) may be included, where each such second zone 300 and/or vessel 310 may function as described herein in conjunction with a first zone 100.

Still further, the exemplary apparatus 10 for treating wastewater may comprise a first zone 100 adapted for receiving a first liquid stream and a first bioreaction zone 130, wherein the first bioreaction zone 130 is configured with one or more first structures 138 for retaining or facilitating growth of one or more first biological microbes and for at least converting organic matter in the first liquid stream into at least volatile fatty acids (VFAs) to produce treated wastewater, and a second zone 300 for receiving the treated wastewater from the first zone 100, said second zone 300 comprising a second bioreaction zone 330 comprising a plurality of second structures 340 configured to facilitate growth of one or more second biological microbes, wherein said plurality of second structures may be electrically conductive for further treating the wastewater and at least converting the VFAs into methane. It should be understood the second zone 300 may be in communication with the first zone 100 to facilitate passage of the one or more microbes in the second zone from the second zone 300 to the first zone 100. The second zone 300 may, or may not be, configured downstream from the first zone 100.

As noted above, the first and second zones may be configured in the same vessel, or in different vessels.

The liquid entering the first zone 100 may be a wastewater stream> However, the first zone 100 may be further adapted to receive a mixed stream comprising previously treated wastewater from the second zone 300 as well, as described further herein.

Sometimes, the first vessel 110 can be suited for anaerobic reactions, such as hydrolysis, acidogenesis, and acetogenesis, although other reactions including methanogenesis may occur. Accordingly, the one or more first structures may comprise a suspended growth retention structure, fixed-film structure such as dynamic media or carrier material, or static media structure, for example. Exemplary suspended growth reactors include a continuously stirred tank reactor, an upflow anaerobic sludge blanket reactor, an expanded granular sludge bed reactor, and an internal circulation reactor.

Suspended growth systems typically include a structure for separating the suspended biomass and biogas from the liquid and retaining the biomass in the reaction zone. Generally, a fixed film reactor contains materials or structures, sometimes fixed or limited in movement, that function to facilitate the growth of biological media. Exemplary anaerobic fixed-film reactors include an anaerobic filter, an anaerobic moving bed bioreactor, and an anaerobic fluidized bed. Additionally, sometimes reactors can be combined into a single vessel, where, for example, an anaerobic biomass functioning as upflow anaerobic sludge blanket in the bottom portion of the reactor and a fixed film process in the upper portion of the reactor. Furthermore, some reactors can include one or more physical membranes for separating various components undergoing anaerobic digestion. Exemplary dynamic media structure or carrier material may comprise small, loosely filled, randomly arranged pieces filling a fraction or all of the zone volume. The media may be made of a plastic material, or alternatively may be made of a glass, ceramic, sand, metal, or carbon material. The media or carriers may be less dense than water or more dense than water. The media may be all of one type, or a mixture of any of the above materials and densities. One type of dynamic media is a plastic, metal, or ceramic Raschig ring or Pall ring. Another type of dynamic media is sand or activated carbon.

A continuously stirred tank reactor may include mechanical or hydraulic mixers to maximize contact between anaerobic biomass and degradable organic compounds. An upflow anaerobic sludge blanket reactor and an expanded granular sludge bed reactor can both include a granular sludge bed or fluidized bed in the lower portion of a reactor. Generally, this granular sludge bed includes naturally occurring microorganisms that form granules, sometimes about 0.5-about 2 millimeters in diameter. Usually, the biomass granules that form a part of the granular sludge bed resists washout, thereby allowing for high hydraulic loads. Exemplary upflow anaerobic sludge blanket and expanded granular sludge bed processes are disclosed in, e.g., US 2014/0367330. Often, an internal circulation reactor includes at least one liquid and gas separator and an internal distribution system for routing liquid, usually water, from one end of the vessel to the other end. Sometimes, wastewater is fed at the bottom of the reactor and a portion from the top is recycled to the bottom. An exemplary internal circulation reactor is disclosed in, e.g., U.S. Pat. No. 5,338,447.

In an exemplary embodiment, the first vessel 110 can be an anaerobic filter reactor, and may comprise a first bioreaction zone 130 separated by a partition 150 from a first compartment 180. The first compartment 180 may be configured to receive treated wastewater exiting the first zone 130 and for transport to the second zone 300. A filter 154 can be coupled to an upper end of the partition 150. The filter 154 can allow water, but not organic masses, to pass into the compartment 180. Sometimes, the first bioreaction zone 130 contains the first structures (e.g., suspended growth, fixed-film structure (e.g., or dynamic packing media or carrier material or statis packing media). In this exemplary embodiment, the bioreaction zone 130 contains an anaerobic filter and a second structure 138, e.g. a packing, although in other exemplary anaerobic embodiments the packing may be omitted, in favor of a different structure, such as an upflow anaerobic sludge blanket reactor. The packing 138 can function to support the growth of a first group of one or more microbes for supporting reactions, although not wanting to be bound by theory, such as hydrolysis, acidogenesis, and acetogenesis. Hydrolysis reactions can be facilitated by microbes such as bacteria from at least one of the genus *Pseudomonas*, *Streptococcus*, and *Clostridium* and the family Enterobacteriaceae. Other microbes, such as acidogens and acetogens can support other reactions to convert organic matter into, e.g., VFA, acetate, carbon dioxide, and hydrogen. The packing 138 can include a plurality of packing media, optionally vertical-flow or cross-flow packing media. Generally, the bioreaction zone 130 may also comprise a manifold 34a operable to receive a biogas stream for mixing and stripping organic growth from first structures within first zones 100 and/or distribute or collect fluid at the top of zone one 100 (when the manifold is located at the top) or at the bottom of zone one 100.

In one embodiment, the manifold 34a can include a plurality of pipes to provide mixing within the first vessel 110. The manifold 34a may be configured to include one or more diffusers or spargers. In some exemplary embodiments, the manifold 34a may include at least about 20, even about 50, or even as much as at least 100 spargers may be used to underlie the packing 138 to provide sufficient conditions for mixing and sheering. Particularly, the biogas can pass through the manifold 34a configured with spargers, mix with the wastewater below the packing 138 and provide turbulence and shearing action within the first vessel 110. Exemplary spargers are disclosed in, e.g., U.S. Pub. No. 2005/0151281. Usually, the manifold 34a is positioned underneath the packing 138.

Figure 2:
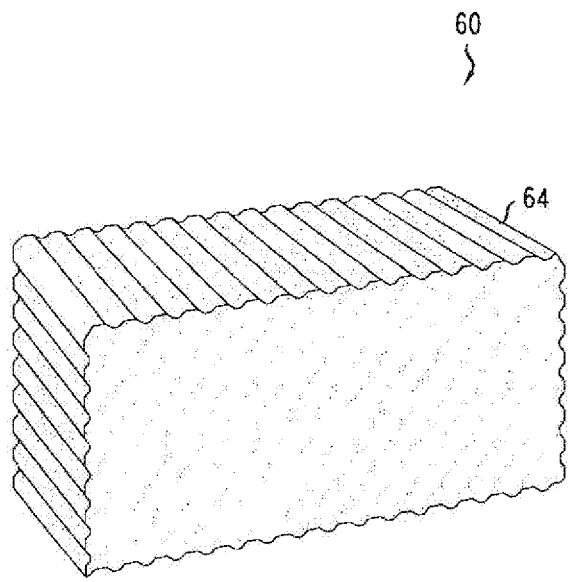
FIG. 2 is a perspective view of an exemplary static packing media.
Figure 3:
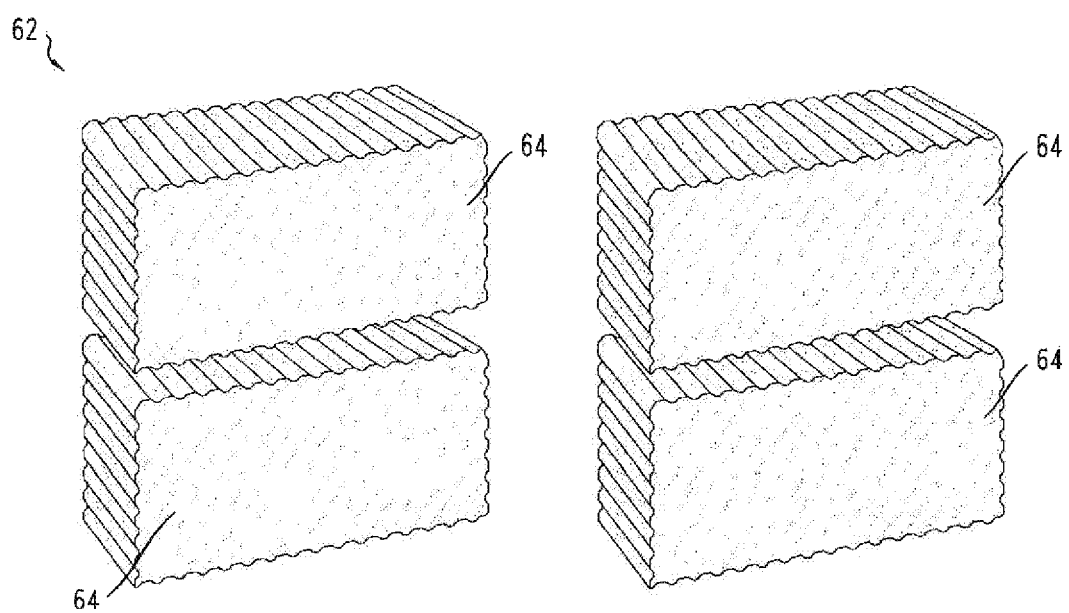
FIG. 3 is a perspective view of a plurality of static packing media.

Referring to FIGS. 2-3, an exemplary vertical flow packing media 60 is depicted that can be arranged to form the packing 138. In this exemplary embodiment, the static packing media 60 can have the form of a block 64 with grooves and recesses that function to facilitate the growth of biological material by increasing the surface area for biological material to anchor and grow. A plurality of static packing media or blocks 62 can be prearranged as stacks in the first vessel 110 before operations. The block 64 can be manufactured from any suitable material, including sheet material disclosed in, e.g., U.S. Pat. No. 5,217,788.

Referring back to FIG. 1, the second vessel 310 in the second zone 300 is in a second position, usually downstream and preferably directly downstream, of the first vessel 110 in a first position, (usually upstream and preferably directly upstream). The second vessel 310 can include a bioreaction zone 330 and a compartment 380, configured to receive wastewater exiting the second zone 300, separated by a partition 350. The bioreaction zone 330 can include vertically arranged electrodes 340 as well (see FIGS. 4 and 6A and 6B)l. Optionally, an insulated spacer or separator may be included between the electrodes (not shown in FIG. 1 but see element 355 in FIGS. 6A and 6B). The plurality of second structures (e.g., electrodes 340) along with any wiring and/or connectors inside of the second vessel 310 can be water proofed with any suitable material, such as a thermoplastic, to seal outside liquids, such as water, to prevent corrosion and rust. Suitable wire insulating materials can include a combination of polyvinyl chloride and polyamides, and/or polytetrafluoroethylene. Often, heat-shrink sleeves are used to protect wire splices. Similarly, the vessels 110 and 310 can be sealed by, e.g., welding, to prevent liquid, e.g., water, seepage.

Moreover, the plurality of electrodes (or conductive structures) 340 can be made of any suitable material that functions to facilitate biological growth and be electrically conductive. Exemplary conductive electrode materials include, but are not limited to, carbon paper, carbon cloth, carbon felt, carbon wool, carbon foam, graphite, porous graphite, graphite powder, graphite granules, graphite fiber, a conductive polymer, a conductive metal, or a combination thereof. Exemplary electrode materials are disclosed in, e.g., U.S. Pat. No. 8,440,438 and U.S. Pub. No. 2015/0147593.

The anode and cathode of each anode/cathode pair can be made of the same material or different materials. Exemplary conductive electrode materials include, but are not limited to, biochar, wire metal mesh, carbon mesh, carbon fiber, carbon granules, carbon paper, carbon cloth, carbon felt, carbon wool, carbon foam, graphite, porous graphite, graphite powder, graphite granules, graphite fiber, a conductive polymer, a conductive metal, and combinations of any of these, as disclosed in, e.g., U.S. Pat. No. 8,962,165. As an example, the anode in at least one of the anode/cathode pairs can be made of a carbon material, such as carbon mesh, carbon cloth, carbon fiber, or carbon felt, while the cathode is any suitable metal mesh. Alternatively, the anode in at least one of the anode/cathode pairs can be a metal mesh, while the cathode is made of a carbon material such as carbon mesh, carbon cloth, carbon fiber, or carbon felt. In certain embodiments, the anode and/or the cathode are made from two or more materials. As a further example, the anode and/or cathode can be made from a combination of a metal and carbon mesh, carbon cloth, carbon fiber, or carbon felt, or a combination of wire mesh and carbon mesh, carbon cloth, carbon fiber, or carbon felt. In one exemplary embodiment, the anode can have a high surface area with a total surface area per volume of the reactor of at least about 9,600 $m^2/m^3$, and in one exemplary embodiment, be a brush anode.

The anode and cathode in each of the anode/cathode pairs can be separated by a means for separating, such as a porous, insulating layer or separator (see element 355 in FIG. 6B, for example), e.g., a plastic material. The porous, insulating layer that separates the anode and cathode can also function to support the anode and cathode in the pairing. As yet another example, the anode and cathode can be painted onto either side of a porous, insulating layer. Optionally, a filter can be included, such as a filter made from biochar, graphite granules, or activated carbon. Electrode holders including spacers and guides can function to facilitate electrode installation. The electrode holders can optionally include combs or guides at the top, bottom, and/or middle and include separator meshes.

Sometimes, the plurality of electrodes 340 may be optionally coated and function to facilitate the growth of methanogenic microbes or methanogens, which may form a biofilm. Often methanogens are archaea, and aceticlastic methanogens, such as of the genera *Methanosaeta* and *Methanosarcina*, metabolize acetate; and hydrogenotrophic methanogens, such as of the orders Methanosarcinales, Methanobacteriales and Methanomassiliicoccales, metabolize hydrogen. Although not wanting to be bound by theory, other methanogens can associate with one or more anode respiring microbes, such as anode respiring bacteria, particularly bacteria from the family Geobacteraceae, and more specifically one or more bacteria from the genus *Geobacter*, and collaborate with the anode respiring bacteria via SAO using direct interspecies electron transfer. Still other methanogens may metabolize a single carbon compound such as methanol and/or methanal and can be referred to as methylotrophs. Still more methanogens may use electrons and protons directly and can be referred to as electromethanogens. Yet still other methanogens may use more than one type of electron source, such as acetate and hydrogen.

The plurality of electrodes 340 provides a current to enhance the growth of microbes that would not dominate vis-à-vis other microbes absent the presence of the electrodes. The production of an electrical current from the electrical potential of the plurality of electrodes can function to facilitate the growth of desired microbes, e.g., anode respiring microbes and/or methanogens, that not only populate the second vessel 310, but the first vessel 110 as hereinafter described, to create a microbe population useful for metabolizing specific compounds, such as VFA.

Moreover, enhancing the diversity of microbes may allow the inventive apparatuses to better withstand process variations in, e.g., pH, temperature, feed composition, and organic loading rate, to maintain lower concentrations of VFA. More diverse apparatuses may be more robust with respect to process variations.

Examples of suitable methanogenic microbes include, but are not limited to, species of the genera *Methanosaeta, Methanosarcina, Methanobacterium, Methanococcus,* and *Methanospirillum*. At least some of these microbes are disclosed in, e.g., U.S. Pub. No. 2013/0299400 referred to previously. Other microbes may include electrically active microbes which transfer electrons to or from the electrodes. These microbes can include, but are not limited to, species of the genera *Geobacter, Pseudomonas,* and *Shewanella,* and species such as *P. putida, S. oneidensis, G. sulfurreducens,* and/or *G. metallireducens.*

Although not wanting to be bound by theory, the direct transfer of electrons between *Geobacter* and *Methanosarcina* genera and between *Geobacter* and *Methansaeta* genera can provide a syntrophic methanogenesis in which VFA consumption by an anode respiring bacterium, e.g. *Geobacter*, is complimented by a direct interspecies electron transfer to a methanogenic species. In this capacity, the impact of *Geobacter* on an anaerobic reactor can be extended beyond the direct current activity of the electrodes. This reaction may provide a syntrophic acetate oxidation bypassing the interspecies hydrogen transfer process and provides an alternative pathway to aceticlastic methanogenesis. This development also represents a novel type of methanogenesis (neither aceticlastic nor hydrogenotrophic nor methylotrophic), which is analogous to cathodic electromethanogenesis. The difference in microbial community composition decreases the dependence on aceticlastic methanogenesis by augmenting syntrophic acetate oxidation. Anode respiring bacteria consume VFA and transfer electrons to electromethanogens via electrodes and via direct interspecies electron transfer. The resulting dominant biochemical reactions favor stability in the anaerobic reactor by facilitating management of VFA and hydrogen. Additionally, nutrients can be added to augment biology in the first and/or second zones 100 and 300.

Figure 4:
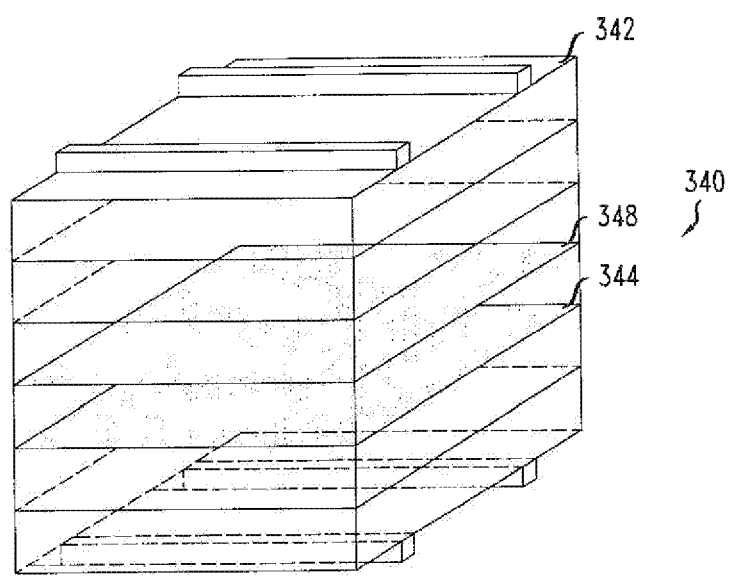
FIG. 4 is a schematic, perspective view of an exemplary electrode rack.

Referring to FIG. 4, an exemplary plurality of electrodes 340 that may be incorporated in to apparatus 10 are depicted. The plurality of electrodes can include at least one anode 344 and at least one cathode 348 inserted into an electrode rack 342. An exemplary electrode rack 342 is disclosed in the '462 application referred to previously. The plurality of electrodes 340 can be placed onto plastic pallets and installed within the second vessel 310. The pallets can remain in the second vessel 310 during operations. In this exemplary embodiment, the plurality of electrodes 340 can be a porous mesh and pallets can have openings that function to permit liquid streams to pass through.

The electrode rack 342 can be oriented in any direction or in any shape or size, as required. In certain embodiments, the rack can be orientated such that the geometric plane of the electrodes is perpendicular to the flow of water to be treated. However, electrodes may also be orientated parallel to the direction of flow or at some angle between parallel and perpendicular. Non-limiting examples of the angles include about 5, 10, 15, 20, 25, 30, 35, 40, 45, 50, 60, 70, 80, or 85 degrees, or in a range bounded by any two of the angles disclosed herein.

Figure 5:
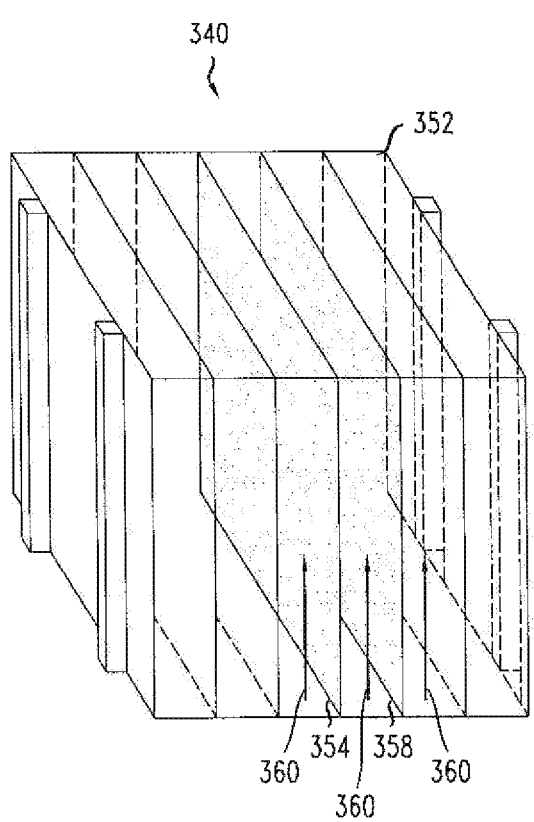
FIG. 5 is a schematic, perspective view of another exemplary electrode rack.

Referring to FIG. 5, another exemplary electrode rack 352 is depicted having a plurality of vertically arranged electrodes 340 with at least one anode 354 and at least one cathode 358 orientated vertically. In this manner, a liquid 360 can flow past, not through, the plurality of electrodes 340. If the plurality of electrodes 340 is installed on a pallet, usually the pallet has openings to permit liquids to flow there-through. Generally, the plurality of electrodes 340 can be made of any suitable material, as described above, including a porous mesh.

Referring back to FIG. 1, the compartment 380 can be adapted to receive the liquid 360 passed by the plurality of electrodes 340. Generated biogas may collect in a head space of the second vessel 310 as a result of metabolic activity. In an embodiment, in operation, sometimes a first liquid stream 90 may be combined with the mixed stream 425 output from the heat exchanger 440, as hereinafter described, to form a combined stream 94 introduced into the first vessel 110 of the first zone 100. The first liquid stream 90 is often a wastewater stream, usually containing organics, and has potential chemical energy. Generally, the combined stream 94 fills the bottom of the first vessel 110 and passes upwards past the packing 138, although flow direction can be in any suitable direction, such as downwards or sideways. A biogas stream 30, as hereinafter described, can enter the manifold 34a and pass through one or more spargers, that are a part of the manifold 34a, and function to mix and strip organic growth from the packing 138.

Sometimes, the combined stream 94 passes through the packing 138 and undergoes various reactions, including creating biogas that can rise in the first vessel 110, accumulate in a head space, and exit as a biogas stream 50. The liquid 192 can collect in the bioreaction zone 130 and pass through the filter 154 in the partition 150 and fall into the compartment 180 having a volume 188. The partially treated wastewater can be withdrawn from the one or more first vessels 110 as a liquid stream 200. The liquid stream 200 can be sent to the one or more second vessels 310 of the second zone 300 and/or by-pass via the second vessel via line 392, depending on the positions (i.e. closed, partially open, or fully open) of valves 394,396. Further, treated water from the one or more second vessels 310 may exit a liquid line and can either be recycled around to the influent of the second vessel 310 or removed as effluent through a liquid line 390 based on the position of valve 398, potentially joining with by-pass line 392, before being either recycled to the one or more first vessels 110 via stream 400 or removed as a system effluent 410, based on the position of control valve 450.

For example, with valve 396 closed and valve 394 open, the stream can pass via line 200 into the second vessel 310. Subsequently, the stream may pass through the bioreaction zone 330 and its plurality of electrodes 340. Usually as the liquid in the stream rises, the liquid is treated and VFA is converted into methane, and other fuel products. The generated biogas can rise, accumulate in a head space, and exit the second vessel 310 as a biogas stream 370. The biogas stream 370 can be combined with the biogas stream 50 to form a combined biogas stream 374. Depending on the state of valve 460 (again, open or closed) the biogas stream 374 can be routed for further treatment, stored, or combusted as a fuel in, e.g., a central heat and power system, and a portion of this stream can be recycled as the biogas stream 30 and pass through the manifold 34a. In sum, the control valve 460 can regulate the amount of the stream 374 that is used as product and the amount that is recycled and used as the biogas stream 30. The biogas may include at least about 50%, about 55%, about 85%, or even about 95%, by volume or by mole, methane. The biogas may also include carbon dioxide, hydrogen sulfide, heavier hydrocarbons, such as propane, one or more siloxanes, and inert gases, such as nitrogen gas.

Backtracking somewhat, alternatively, when the valve 372 is closed, the biogas stream 370 may be recirculated back to the second vessel 310 via biogas recirculation line 373. Optionally, the recirculated biogas stream may be input into a second manifold 34b. The second manifold 34b may be operable to receive the biogas stream for mixing contents of the second zone and/or distribute or collect fluid at the top of zone two 300 (when the manifold is so located at the top) or at the bottom of zone two 300. The second manifold may comprise a plurality of pipes to provide mixing within the second vessel 310. The manifold 34b may be configured to include one or more diffusers or spargers. In some exemplary embodiments, the manifold 34b may include at least about 20, even about 50, or even as much as at least 100 spargers to provide sufficient conditions for mixing. It should be understood that manifolds 34a and 34b may be a single manifold.

Usually, the liquid 360 passes past the plurality of electrodes 340 and over the partition 350 into the compartment 380. The liquid 360 can exit as an effluent 390 and pass downstream as a product stream 410. Usually, at least a portion 400 of the stream 410 can be recycled by passing through the inline mixer 420 and combined with an alkaline stream 40, sometimes a sodium hydroxide solution. Alternatively, the valve 398 may be closed, thereby causing the effluent to return to the second vessel 310 via recirculation line 399.

Generally, in the exemplary apparatus 10 the pH and temperature in the first zone 100 and second zone 300 may be maintained at the same levels, e.g., a pH of between 5 and 9, and a temperature between 80 F and 105 F. Alternatively, the pH and temperature of each zone may differ. For example, the pH in the first zone 100 may be between 5 and 7 and the temperature between 15° C. and 41° C., while the pH in the second zone may be between 6.5 and 7.5, and a temperature between 35° C. and 38° C.

Further, the pH may be adjusted to about 6-about 8, desirably about 6.5-about 7.5, and more desirably about 7.2. Usually, the alkaline solution is about 30-about 50%, by weight, alkaline in water based on the total weight of the solution. Any suitable alkaline may be used, such as potassium hydroxide, magnesium hydroxide, calcium hydroxide, sodium carbonate, potassium carbonate, calcium carbonate, ammonia, or any combination thereof. If acid is added to correct pH, any suitable acid may be used, such as hydrochloric, phosphoric, sulfuric, or nitric acid, or any combination thereof, in any suitable amount to adjust the pH.

Afterwards, a mixed stream 424 can pass through the heat exchanger 440 and be warmed to about 30-about 45° C., or even about 35-about 38° C. Usually, a heated water stream 444 is used to heat the mixed stream 424, which then forms stream 425 that is combined with the first liquid stream 90. A control valve 450 can regulate the amount of the product stream 410 and recycle stream 400.

Sometimes, the recycle stream 400 provides a passage for introducing one or more microbes from the second vessel 310 into the first vessel 110. This introduction may transfer methanogenic microbes that can function to facilitate reactions in the first vessel 110, and further the metabolization of VFA. Often, the first vessel 110 and second vessel 310 may have, independently, an exemplary, non-limiting headspace pressure of about 90,000-about 110,000 Pa and a temperature of about 30-about 45° C.

Flow distribution through the first and second zones 100 and 300 can be augmented with slits in, or larger openings in, vessels receiving flow. Also, optionally one or more overflow weirs may be positioned at the top of a vessels before liquid enters piping (see elements 361a to c in FIG. 6A, for example) for distributing energy in the received liquid (e.g., wastewater).

The second zone 300 can include a brush or scrapper (not shown in FIG. 1) to clean the plurality of electrodes 340 of organic growth. Alternatively, a sparge gas from manifold 34b comprised of fine or course bubbles can be utilized or liquid spray jets for cleaning the plurality of electrodes 340.

If maintenance is required on the second vessel 310, such as inspecting and/or repairing the plurality of electrodes 340, the second vessel 310 can be bypassed by closing the valve 394 and opening the valve 396. Additional valves may also be incorporated and function to isolate the second vessel 310, such as by closing valve 398. In this manner, operations can be conducted with the first vessel 110 by routing the stream 200 as a bypass stream 392, while maintenance is being conducted on the second vessel 310. Once maintenance and/or repairs are completed on the second vessel 310, the valves 394 and 398 can be opened and the valve 396 closed, routing the stream 200 to the second vessel 310.

Figure 6A:
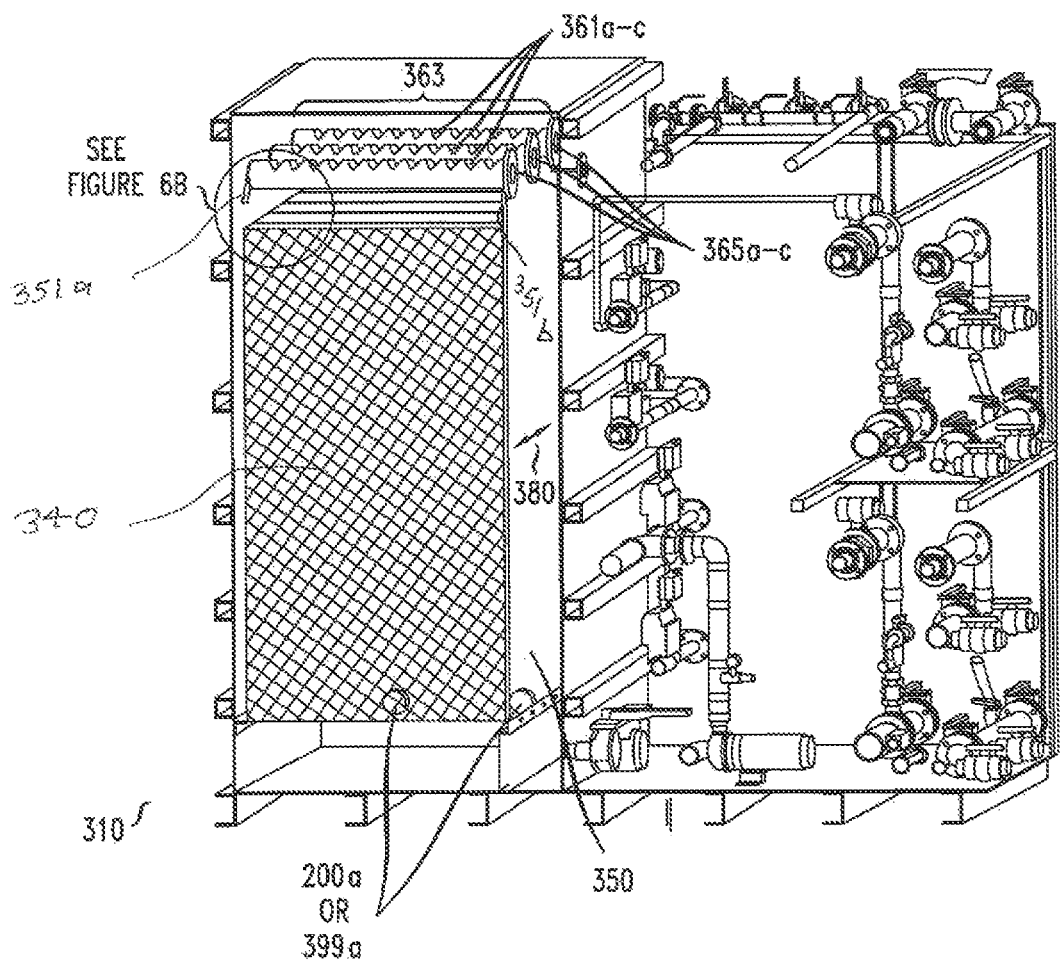
FIGS. 6A and B depict views of an exemplary vertical electrode configuration according to embodiments of the invention.

Referring now to FIG. 6A, there is depicted an exemplary configuration of a second vessel 310 that comprises a plurality of second structures 340, 355, e.g. vertical arranged electrodes 340, and insulated separators 355. One example of an insulated separator is a plastic mesh.

Figure 6B:
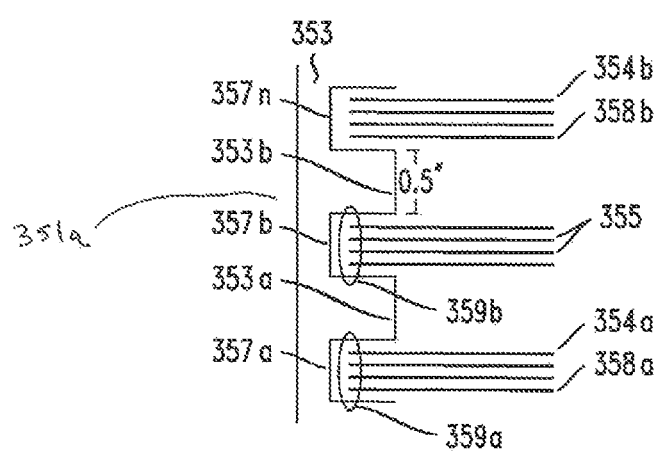

Referring now to FIG. 6B, one or more of the electrodes 340 may comprise either an anode or a cathode, represented by anode 354a or cathode 358a in FIG. 6B. Together, one anode and one cathode comprise an electrode pair. In one non-limiting embodiment, the number of pairs may be sixty, though, again this is merely exemplary. Further, as depicted in FIG. 6B, to retain and support the second structures the second zone 300 may comprise one or more guidepieces 351a-n (where "n" is the last guidepiece) for retaining one or more second structures (e.g., electrodes, porous mesh) of the plurality of second structures, where one or more of the guidepieces 351a-n may comprise additional structure configured to retain and remove one or more of the second structures.

In FIG. 6B, one or more means for separating ("separators" for short) 355 may be configured to be received by the guidepiece 351a such that a given insulated separator 355 is positioned between pairs of electrodes (e.g., between electrode pair 354a,358a and pair 354b, 358b).

In accordance with the embodiments depicted in FIGS. 6A and 6B, each of the electrodes 340 and each of the separators 355 may be configured to be received by guidepieces 351a,b. For the sake of simplicity only a single guidepiece 351a is shown in FIG. 6B, though it should be understood the that second vessel 310 includes at least two guidepieces on opposite ends of the of electrodes 340. It should be further understood that although the features of a single guidepiece 351a are described herein, each guidepiece 351a,b includes similar features unless otherwise noted herein. Each of the guidepieces 351a,b may have a vertical length that equals the vertical length of a second structure. In the embodiment depicted in FIGS. 6A and 6B, that second structure is an electrode(s), such as electrode 340. In one embodiment, the length of an electrode 340 may be 8 feet.

More particularly, as shown in FIG. 6B, the guidepiece 351a comprises one or more vertically configured slots 357a, 357b . . . n (where "n" represents the last slot) for receiving and restraining electrodes 340 (e.g., anodes 354a, 354b and cathodes 358a, 358b) and/or separators 355. In an embodiment, a slot 357a, b . . . n may be configured in a shape to receive a complimentarily shaped electrode side portion 359a, b . . . n or a side portion of a separator 355. Once received (inserted) the electrode or separator may be slid vertically into the entire length of the slot 357a, b, . . . n which may be as long as the received (e.g., inserted) electrode or separator (e.g., 8 feet in length). Accordingly, the slots 357a, b . . . n function to substantially restrain the horizontal and angular movement of each of the electrodes 340 and separators 355.

In an embodiment, each of the electrodes 340 (e.g., anodes 354a, 354b and cathodes 358a, 358b) and separators 355 are of a sufficient weight so that they are retained within their respective slots 357a, b . . . n without the need for additional retaining means. Alternatively, the guidepieces 351a,b may include additional structure configured to retain or remove one or more of the second structures or separators (e.g., to allow a received electrode or separator to be retained and removed). Some examples of additional structure are e.g., clips, pressure sensitive bindings, clamps.

In an embodiment, the guidepiece 351a may further comprise a means for separating 353a, b . . . n each of the second structures (e.g., electrodes) 340 or separators 355 ("guidepiece separating means" for short) and one or more of the slots 357a, b . . . n. In one example, each guidepiece separating means 353a, b . . . n may comprise a section of the guidepiece 351a that protrudes substantially perpendicular from a main section 353 of the guidepiece 351a. Further, the dimensions of a guidepiece separating means 353a, b . . . n may comprise a dimension (width) that separates one second structure (electrode) and/or separator 355 from another second structure (e.g. electrode), and optimizes the flow of treated wastewater through the second vessel 310. For example, the width of a guidepiece separating means 353a, b . . . n may comprise 0.50 inches. In one embodiment, the width of a slot 357a, b . . . n may also be 0.50 inches, for example. In an embodiment, the length of the guidepiece separating means may be the same as the length of a slot 357a, b . . . n or electrode 340 (e.g., 8 feet).

Wastewater may flow from the first vessel 110 into the second vessel 310 via openings 200a or 399a (associated with lines 200 and 399 shown in FIG. 1), and then up past the electrodes 340 and into to the underside of the weirs 361a-c. Thereafter, the wastewater may flow up past the outside of the weirs 361a-c to the top of the weirs 361a-c, and then enter the holes, orifices or notches 363 in the top of the weirs 361a-c and into the weirs 361a-c (i.e., into the piping). The wastewater may then flow through the weirs 361a-c and exit out of the outputs 365a-c into a standpipe structure 380 that is operable to accumulate and hold liquid for pumping to a next location.

It should be understood that each of the orifices 363 function to apply a force to, and distribute energy in, the flowing wastewater.

Figure 7A:
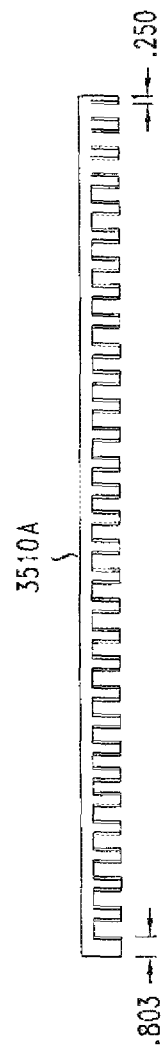
FIGS. 7A-D depict views of exemplary electrode guidepieces according to embodiments of the invention.
Figure 7B:
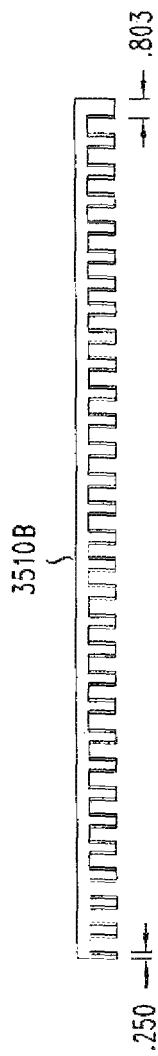
Figure 7C:
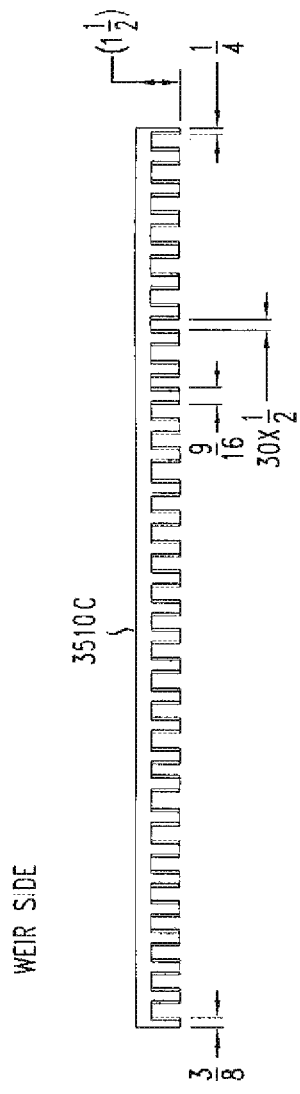
Figure 7D:
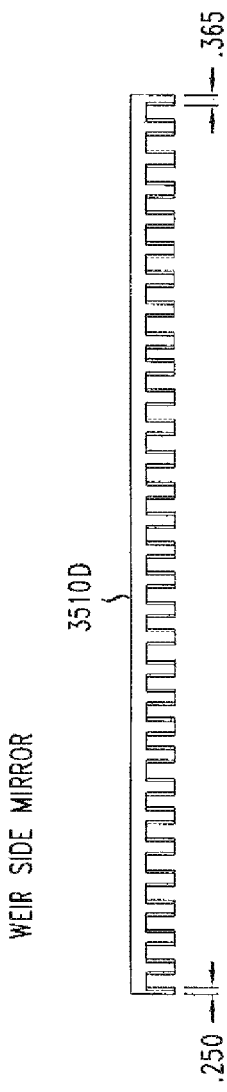

In one embodiment the guidepiece 351a (or 351b) may comprise a multipiece element (e.g., two elements). For example, FIGS. 7A and 7B depict guidepieces 3510a and 3510b that may comprise guidepiece 351a located on an end of the electrodes that is opposite the weirs 361a-c (thus the name "not-weir side"). Similarly, guidepieces 3510c and 3510d depicted in FIGS. 7C and 7D may be located on an end of the electrodes that is on the same side as weirs 361a-c (thus the name "weir side") and may form guidepiece 351b.

As previously mentioned, and now reiterated, the dimensions set forth in FIGS. 6A through 7D, as well as in all of the figures, are merely exemplary, and non-limiting and are provided to give those skilled in the art examples of the relative dimensions of each respective element.

Figure 8:
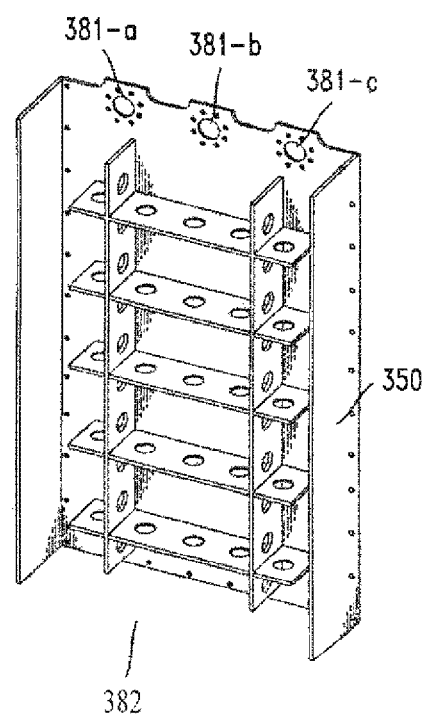
FIG. 8 depicts an exemplary support structure that may be used in combination with other inventive structures according to an embodiment of the invention.

Referring now to FIG. 8 there is depicted a support structure 382 that may be integral to standpipe 380. As depicted, the support structure 382 may comprise the partition (or wall) 350 of the standpipe 380. The support structure 382 may comprise a plurality of openings 381a to c, where each of the openings are configured to received one of the weir outputs 365a-c (see FIG. 6A). The structure 382 may be inserted adjacent the second vessel 310. Alternatively, the structure 382 may be integral with a wall of the second vessel 310 or standpipe 380.

In those instances where the pressure exerted by wastewater within the second vessel 310 may exceed the pressure exerted by wastewater within the standpipe 380, the structure 382 functions to provide support for the external wall of the second vessel 310, as well as functioning as a wall of the standpipe 380, where it should be understood that the external wall of the second vessel and standpipe wall may be one and the same structure.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever. Further, it should be understood that one or more features of one exemplary apparatus and/or process may be combined with one or more features of another exemplary apparatus and/or process to form additional apparatuses and/or processes.

From the foregoing description, one skilled in the art can easily ascertain the essential characteristics of this invention and, without departing from the spirit and scope thereof, can make various changes and modifications of the invention to adapt it to various usages and conditions.

We claim:

1. An apparatus for treating wastewater comprising:
   a first zone adapted to receive a mixed stream comprising previous, anaerobically treated wastewater from a second zone, wherein the previous, anaerobically treated wastewater facilitates direct transport and passage of one or more second biological microbes from the second zone to the first zone, said first zone comprising a first bioreaction zone, wherein the first bioreaction zone is configured with one or more retaining or facilitating structures that retain or facilitate growth of one or more first biological microbes and convert organic matter in a first liquid stream or a combination of the first stream and the mixed stream into at least carbon dioxide to produce treated wastewater;
   a second zone adapted to receive the treated wastewater from the first zone, said second zone comprising a second bioreaction zone comprising a plurality of anaerobically facilitating structures configured to anaerobically facilitate growth of one or more second biological microbes; and
   wherein said plurality of anaerobically facilitating structures comprise a pair of electrodes comprising both an anode and a cathode configured to further treat the wastewater and at least convert the carbon dioxide into methane.

2. The apparatus as in claim 1 wherein the first and second zones are configured in a same vessel.

3. The apparatus as in claim 1 wherein the first and second zones are configured in different vessels.

4. The apparatus as in claim 1 further comprising first means for mixing or fluidizing biomass or dynamic media structures in the first zone.

5. The apparatus as in claim 4 wherein the first means for mixing or fluidizing comprises means selected from the group comprising a mechanical mixer, liquid recirculation mixer, or gas mixer.

6. The apparatus as in claim 1, further comprising second means for mixing in the second zone.

7. The apparatus as in claim 6 wherein the second means for mixing comprises liquid recirculation flow structure or a gas mixer.

8. The apparatus as in claim 1 further comprising a manifold operable to distribute or collect fluid at the top of the first zone or at the bottom of the first zone.

9. The apparatus as in claim 1 further comprising a manifold operable to distribute or collect fluid at the top of the second zone or at the bottom of the second zone.

10. The apparatus as in claim 1 further comprising a manifold for receiving a biogas stream for mixing and stripping organic growth from the plurality of anaerobically facilitating structures.

11. The apparatus as in claim 1, wherein the second zone is configured downstream from the first zone.

12. The apparatus as in claim 1, wherein the plurality of anaerobically facilitating structures are vertically arranged.

13. The apparatus as in claim 1, wherein the the plurality of anaerobically facilitating structures comprise a porous mesh.

14. The apparatus as in claim 1, wherein the second zone is in communication with the first zone to facilitate passage of the one or more second biological microbes in the second zone from the second zone to the first zone.

15. The apparatus as in claim 1, wherein the second zone further comprises one or more guidepieces for retaining one or more of the plurality of anaerobically facilitating structures.

16. The apparatus as in claim 15, wherein one or more of the guidepieces comprises additional structure configured to retain and remove one or more of the plurality of anaerobically facilitating structures.

17. An apparatus for treating wastewater comprising:
   a first zone adapted to receive a mixed stream comprising previous, anaerobically treated wastewater from a second zone, wherein the previous, anaerobically treated wastewater facilitates direct transport and passage of one or more second biological microbes from the second zone to the first zone, said first zone comprising a first bioreaction zone, wherein the first bioreaction zone is configured with one or more retaining or facilitating structures that retain or facilitate growth of one or more first biological microbes and convert organic matter in a first liquid stream or a combination of the first stream and the mixed stream into at least hydrogen to produce treated wastewater;
   a second zone adapted to receive the treated wastewater from the first zone, said second zone comprising a second bioreaction zone comprising a plurality of anaerobically facilitating structures configured to anaerobically facilitate growth of one or more second biological microbes; and
   wherein said plurality of anaerobically facilitating structures comprise a pair of electrodes comprising both an anode and a cathode configured to further treat the wastewater and at least convert the hydrogen into methane.

18. The apparatus as in claim 17, wherein the one or more retaining or facilitating structures comprises a suspended growth retention structure or fixed-film structure.

19. An apparatus for treating wastewater comprising:

a first zone adapted to receive a mixed stream comprising previous, anaerobically treated wastewater from a second zone, wherein the previous, anaerobically treated wastewater facilitates direct transport and passage of one or more second biological microbes from the second zone to the first zone, said first zone comprising a first bioreaction zone, wherein the first bioreaction zone is configured to produce treated wastewater;

a second zone adapted to receive the treated wastewater from the first zone, said second zone comprising a second bioreaction zone comprising a plurality of anaerobically facilitating structures configured to anaerobically facilitate growth of one or more second biological microbes; and wherein said plurality of anaerobically facilitating structures comprise a pair of electrodes comprising both an anode and a cathode configured to further treat the wastewater.

20. An apparatus for treating wastewater comprising:

a first zone adapted to receive a mixed stream comprising previous, anaerobically treated wastewater from a second zone, wherein the previous, anaerobically treated wastewater facilitates direct transport and passage of one or more methanogenic microbes or methanogens from the second zone to the first zone, said first zone comprising a first bioreaction zone, wherein the first bioreaction zone is configured to produce treated wastewater;

a second zone adapted to receive the treated wastewater from the first zone, said second zone comprising a second bioreaction zone comprising a plurality of anaerobically facilitating structures configured to anaerobically facilitate growth of the one or more methanogenic microbes or methanogens; and wherein said plurality of anaerobically facilitating structures comprise a pair of electrodes comprising both an anode and a cathode configured to further treat the wastewater.

* * * * *